United States Patent [19]

Van der Salm

[11] Patent Number: Plant 7,274

[45] Date of Patent: Jul. 17, 1990

[54] LILIUM ANTARCTICA

[76] Inventor: Gerardus C. Van der Salm, Rte. 4, Box 422, Woodland, Wash. 98674

[21] Appl. No.: 350,123

[22] Filed: May 10, 1989

[51] Int. Cl.[5] ..... A01H 5/00

[52] U.S. Cl. ..... Plt./68

[58] Field of Search ..... Plt./68

*Primary Examiner*—James R. Feyrer

*Attorney, Agent, or Firm*—Klarquist, Sparkman, Campbell, Leigh & Whinston

[57] ABSTRACT

A new variety of hybrid lily plant bearing large clusters of flowers of excellent form and long persistence, both on the plant and as cut flowers. The up-facing flowers of the new plant are particularly characterized by their truly white flowers with a slight flush of green extending from the nectaries and by their narrow ring of tiny deep magenta spots in the center of the flower. This combination is completely new in the upright Asiatic divisions of lilies suited to forcing and to mass commercial cultivation. The plant is highly resistant to disease and shows high tolerance of virus. The plant also is an excellent garden plant. The bulbs may be pre-cooled and forced for cut-flower production. The new variety is vigorous and is a good grower and propagator.

1 Drawing Sheet

BACKGROUND OF THE INVENTION

My new variety of hybrid lily plant originated as a seedling selected from a group of seedlings at Julianadorp, the Netherlands. The seedlings were planted as a result of breeding efforts carried on by me since 1976; the final cross that produced my new variety, which I call Antarcitica, was made in 1982. The breeding efforts had as their objective the production of truly white upright Asiatic lilies with a high bud count, well suited to forcing for cut-flower production out of season, heretofore unknown in the lily breeding art.

I achieved the desired objective by extensive interpollinations among many hybrid lily cultivars.

The flowers of my new lily are characterized by an upright orientation, true white color, slight flush of green at the nectaries, and a narrow ring of tiny deep magenta spots in the center of the flower, unique in Asiatic hybrid lilies. In addition, my new variety possesses to a high degree the desirable characteristics of hybrid vigor, hardiness, and disease resistance. My new variety also possesses the desired characteristics of excellence of form, color, and habit. The flowers of my new variety are of large size and are produced on a single stalk. My Antarctica variety is vigorous and a good grower and propagator, as observed at Julianadorp, the Netherlands, and at Woodland, Wash.

My new variety is also well suited to forcing out of season when the bulbs are dug at the appropriate time and properly precooled.

My new variety of lily plant has been asexually reproduced by me and under my direction at Julianadorp, the Netherlands and at Woodland, Wash. Successive generations produced by bulb scale propagation and by natural propagation from bulblets have demonstrated that the novel and distinctive characteristics of my new variety are fixed and hold true under asexual propagation from generation to generation.

BRIEF DESCRIPTION OF THE DRAWINGS

My new variety of lily plant is illustrated in the accompanying photographic drawing, which shows the open bloom in full color and illustrates the flower form, the tepal form and arrangement, the connection of the flower to the stem, and in particular the novel and distinctive truly white flowers with a slight flush of green at the nectaries and with a narrow ring in tiny, deep magenta spots in the center of the flowers only.

DETAILED DESCRIPTION OF MY NEW VARIETY

The following is a detailed description of my new variety of Asiatic hybrid lily, with nomenclature according to the International Lily Register (Royal Horticultural Society of London, England, Second Edition, 1969), and with color designations according to the Colour Chart of The Royal Horticultural Society, published by the Society in 1966.

The Plant

Origin: Seedling.

Seed parent: Unnamed seedling.

Pollen parent: Unnamed seedling.

Commercial classification: Hybrid Lilium clone.

Horticultural classification: Division I-A, upright Asiatic hybrid lily, according to the Horticultural Classification of Lilies, Royal Horticultural Society of London.

Form: Single stem, erect and stately.

Height: 70 to 100 cm from bulbs 15 to 18 cm in circumference, provided their light levels are adequate; low light levels may case "stretching".

Growth: Vigorous and upright.

Foliage quantity: Abundant.

Size of leaf: Averages 8 to 12 cm long×5 to 12 mm wide.

Shape of leaf: Lanceolate (pointed).

Texture: Leathery and glossy. Apex of leaves may be lightly pubescent.

Color: Dark green, lighter on lower side.

Bulb size: Any size, ranging to 25 cm circumference commercially.

Bulb color: White.

The Bud

Form: Obtuse, ovoid, and long.

Size: 8 to 9 cm long and 7 cm in circumference just prior to opening.

Opening: Bud opens slowly, in response to morning light; this takes about one hour.

Color: Soft green changing to palest cream or white, overlaid with light plum along the midrib just prior to opening.

Penduncle: Averages 4 to 6 cm, but it may elongate if light levels are too low or if bulbs have been improperly stored prior to forcing. Color is dark green with plum overlay.

The Flower

Blooming habit: Annually in midseason; flowers once and profusely.

Size: Flowers are large-sized for Asiatic hybrids. The flowers average 14 to 17 cm in diameter; the outer tepals average 2 to 2.5 cm wide, and the inner tepals average 3 cm wide.

Borne: In a single racemic inflorescence producing 7 to 12 buds (from a bulb 18 cm in circumference).

Shape: First open in cup shape, which flattens slightly as tepal tips recurve somewhat by their second day.

Tepalage: Typical of genus Lilium, with 6 imbricated tepals.

Tepal color: Flowers are distinguished by their pure white coloration, with a slight flush of soft green (2 mm wide) extending 2–3 mm from the nectaries. Under hot conditions, this green fades and vanishes as the flower opens.

Tepal spotting: Tepals have a narrow ring (1 cm wide) of tiny, deep magenta spots at the center of the flower, encircling the nectaries. The spots are unusually small and inconspicuous.

Tepal longevity: Tepals stay on stems about three weeks.

Pedicel length: Average 6 to 12 cm long.

Pedicel color: Deep green with plum overlay.

Pedicel form: Sturdy and ascending up to 45 degrees from the horizontal. Occasional secondary buds.

Color changes: Very slight. Cool conditions may deepen the soft plum coloration along the midribs on the outside of the tepals, especially before the buds open; extreme heat or light may diminish this anthocyanin pigment and cause the bud to be completely white even along the midribs.

Appearance: Flower is shiny.

Disease resistance: The flower and plant are resistant to disease; in particular, they are resistant to Fusarium bulb rot and Botrytis blight.

Fragrance: None.

Lasting quality: The flower is long lasting, both on the plant and as a cut-flower.

The Reproductive Organs

Stamens and Anthers: Arrangement typical of genus Lilium. Six stamens with white or palest green filaments 5 cm long. Pollen and anthers (dehisced): Pollen is R.H.S.C.C. greyed red 187A.

Pistil: One in number, 5 cm long.

Stigma: Plum colored, medium in size.

Characteristics of ovary: Characteristic of genus Lilium.

The Fruit

Fertility: The fruit is fertile.

Shape: Ovoid.

Color at maturity: Soft brown, sometimes overlaid with soft plum.

My new variety of Asiatic hybrid lily most nearly resembles "Mt. Blanc." Although Mt. Blanc is white under high light conditions it is more cream to light yellow in color, in comparison to the true white of my new variety, under winter or low light growing conditions. Also, the vase life of my new variety is much longer than the vase life of Mt. Blanc flowers, apparently due to the thicker petals of my new variety in comparison to the petals of Mt. Blanc.

I claim:

1. A new and distinctive variety of Asiatic hybrid lily plant substantially as herein shown and described, characterized by its truly white upfacing flowers with a slight flush of green extending from the nectaries and narrow ring of deep magenta spots in the center of the flower.

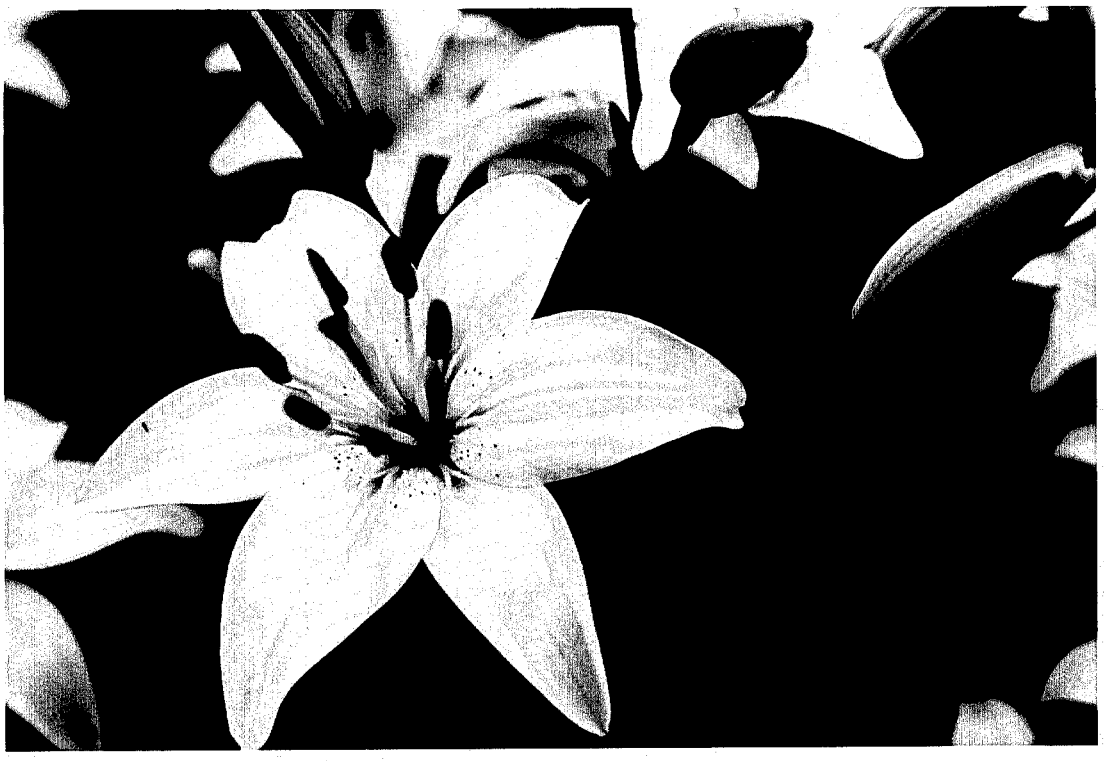

* * * * *